(12) United States Patent
Bowman et al.

(10) Patent No.: US 7,838,571 B2
(45) Date of Patent: Nov. 23, 2010

(54) PHOTOPOLYMERS AND USE IN DENTAL RESTORATIVE MATERIALS

(75) Inventors: Christopher N. Bowman, Boulder, CO (US); Hui Lu, Dover, DE (US); Jeffrey W. Stansbury, Centennial, CO (US)

(73) Assignee: The Regents of the University of Colorado, Denver, CO (US)

( * ) Notice: Subject to any disclaimer, the term of this patent is extended or adjusted under 35 U.S.C. 154(b) by 412 days.

(21) Appl. No.: 10/576,635

(22) PCT Filed: Oct. 22, 2004

(86) PCT No.: PCT/US2004/034968

§ 371 (c)(1),
(2), (4) Date: Apr. 21, 2006

(87) PCT Pub. No.: WO2005/041807

PCT Pub. Date: May 12, 2005

(65) Prior Publication Data

US 2007/0082966 A1    Apr. 12, 2007

(51) Int. Cl.
*A61K 6/087* (2006.01)
*A61K 6/08* (2006.01)
*C08G 75/00* (2006.01)

(52) U.S. Cl. .......................... 522/44; 522/48; 522/167; 522/180; 523/115; 523/116

(58) Field of Classification Search ............... 522/44, 522/48, 83, 180; 523/116, 115
See application file for complete search history.

(56) References Cited

U.S. PATENT DOCUMENTS

| | | | |
|---|---|---|---|
| 4,536,523 A | 8/1985 | Antonucci | |
| 5,100,928 A * | 3/1992 | Grosso et al. | 522/25 |
| 5,100,929 A | 3/1992 | Jochum et al. | |
| 5,554,665 A | 9/1996 | Tateosian et al. | |
| 5,889,132 A * | 3/1999 | Rheinberger et al. | 526/279 |
| 6,310,161 B1 | 10/2001 | Weissman | |
| 6,384,107 B2 | 5/2002 | Liu et al. | |
| 6,479,622 B1 | 11/2002 | Gross et al. | |
| 2007/0082966 A1 | 4/2007 | Bowman et al. | |
| 2007/0185230 A1* | 8/2007 | Bowman et al. | 523/115 |
| 2009/0047633 A1 | 2/2009 | Huo et al. | |
| 2009/0270528 A1* | 10/2009 | Bowman et al. | 523/116 |

FOREIGN PATENT DOCUMENTS

JP    01 026505 A    1/1989

OTHER PUBLICATIONS

International Search Report and Written Opinion of the International Searching Authority dated Mar. 31, 2005.

(Continued)

*Primary Examiner*—Susan W Berman
(74) *Attorney, Agent, or Firm*—Merchant & Gould

(57) ABSTRACT

Photopolymerizable polymer composites based on dimethacrylate systems have been increasingly utilized as dental restorative materials. One of the biggest drawbacks of current dental resin systems is the volume shrinkage and shrinkage induced stresses that arise during the polymerization. Other major problems include incomplete double bond conversion and insufficient wear resistance. This invention involves the development of an entirely novel approach to the photopolymerization process that utilizes thiol-ene systems as low shrinkage and ultra-low shrinkage stress dental restorative materials. Compared with the traditional dimethacrylate dental resins, these novel photopolymerizations have demonstrated a dramatically decreased volume shrinkage, extremely rapid polymerization, abilities to photopolymerize ultrathick materials and achieve much higher conversion, lack of oxygen inhibition and ultra-low shrinkage stress due to low volume shrinkage and drastically delayed gel point conversion. These polymers have thus shown outstanding suitability as dental restorative materials.

12 Claims, 8 Drawing Sheets

OTHER PUBLICATIONS

International Preliminary Report on Patentability from the International Bureau dated Apr. 24, 2006.
Supplementary European Search Report, Apr. 22, 2009, concerning European Patent Application No. 04796032.3.
Database WPI Week 198910, Thomson Scientific, London, GB; AN 1989-073385; XP002523635.
International Search Report re: PCT/US10/28647 mailed May 10, 2010.

* cited by examiner

PHOTOPOLYMERS AND USE IN DENTAL RESTORATIVE MATERIALS

STATEMENT REGARDING FEDERALLY SPONSORED RESEARCH OR DEVELOPMENT

The invention was sponsored by NIH Grant No. DE 10959-05 and the government has certain rights to this invention.

FIELD OF THE INVENTION

The present invention relates to a thiol-ene polymer system with high conversion and more particularly to a thiol-ene polymer system for use as a dental restorative resin.

BACKGROUND

Currently, commercial photoactivated dental restorative resins are based on dimethacrylates and the reaction mechanism is through chain-growth free radical polymerization. Existing dimethacrylate systems are popular for fillings and other dental prostheses because of their esthetic merit and "cure-on-command" feature.

Such dental restorative materials are often mixed with 45 to 85% by weight (wt %) silanized filler compounds such as barium, strontium, zirconia silicate and/or amorphous silica to match the color and opacity to a particular use or tooth. The filler is typically in the form of particles with a size ranging from 0.01 to 5.0 micrometers.

The photoactivated restorative materials are often sold in separate syringes or single-dose capsules of different shades. If provided in a syringe, the user dispenses (by pressing a plunger or turning a screw adapted plunger on the syringe) the necessary amount of restorative material from the syringe onto a suitable mixing surface. Then the material is placed directly into the cavity, mold, or location of use. If provided as a single-dose capsule, the capsule is placed into a dispensing device that can dispense the material directly into the cavity, mold, etc. After the restorative material is placed, it is photopolymerized or cured by exposing the restorative material to the appropriate light source. The resulting cured polymer may then be finished or polished as necessary with appropriate tools. Such dental restoratives can be used for direct anterior and posterior restorations, core build-ups, splinting and indirect restorations including inlays, onlays and veneers.

Although easy to use, these systems have several drawbacks, primarily associated with the polymerization volume shrinkage and shrinkage stress, and poor conversion of the dimethacrylate systems' monomers into polymer. The current systems can only reach a final double bond conversion of 55 to 75%, which not only contributes to the insufficient wear resistance and mechanical properties, but also jeopardizes the biocompatibility of the composites due to the leachable unreacted monomers. Dimethacrylate based resins exhibit significant volumetric shrinkage during polymerization and the induced shrinkage stress results in tooth-composite adhesive failure, initiating microleakage and recurrent caries, which significantly reduces the longevity and utility of current dental restorative composite. Furthermore, as one tries to increase the final double bond conversion to reduce the unreacted monomers, the volumetric shrinkage and shrinkage stress unfortunately also increase, which has been a persisting problem since the development of this class of resins.

Yet another drawback associated with the current systems is odor. Because the polymers are polymerized in the mouth, odors are highly perceptible by the patient. Dimethacrylate based systems, due to the low conversion, after polymerization experience a high amount of leaching of unreacted monomers, which results in an unwanted and offensive taste and odor for some period of time after the procedure.

SUMMARY OF THE INVENTION

The present invention can be thought of as a thiol-ene polymer system with a high conversion, low shrinkage and low shrinkage stress during curing. The thiol-ene system for use in making dental prosthetics having 10%-90% by weight of its functional groups as thiol functional groups (—SH) is disclosed. The thiol-ene system preferably has 10%-90% by weight of its functional groups as thiol functional groups, more preferably 15%-60% by weight thiol functional groups and even more preferably 45%-55% by weight thiol functional groups. In some embodiments, the balance of the functional groups in the system may consist of vinyl groups or may be a combination of vinyl groups and other functional groups.

Prior art dental restorative resins are based on dimethacrylates that use a chain-growth free radical polymerization mechanism. The thiol-ene polymerization proceeds through a totally different route: step growth polymerization facilitated by rapid and facile chain transfer. Besides the impact of the polymerization mechanism on the gel point conversion and network formation, the thiol-ene systems have demonstrated decreased volume shrinkage and shrinkage stress during polymerization.

Thiol-ene polymerization has demonstrated dramatically reduced volume shrinkage, which hasn't been reported previously in the literature.

Thiol-ene polymerizations have a significantly increased gel point conversion, which, together with the low shrinkage, results in ultra-low shrinkage stress. This feature is extremely beneficial to the dental restorative composite applications, which cannot be achieved by any current free radically polymerized dental resin systems.

The oligomerization of thiol-ene monomers will further reduce the polymerization shrinkage. In addition, elimination of low molecular weight reactants during oligomerization will result in dental resins with less odor than current methacrylate based systems.

Due to the mechanisms of the thiol-ene polymerization and the high conversion that has been achieved in the preliminary experiments, thiol-ene polymers contain much less unreacted monomer that can be leached out into the oral environment. This has been confirmed with the solvent extraction experiments conducted on commercial thiol-ene systems.

The thiol-ene polymerization has demonstrated much thicker curing depth than methacrylate based resin systems. This will greatly reduce the patient's chair-time since one-step curing is feasible, especially for large cavity filling, where incremental filling has to be applied using current dental composite systems.

Reduced volume shrinkage during polymerization and the dramatically reduced shrinkage stress due to the reduced volume shrinkage and significantly delayed gel point conversion. These features will greatly alleviate the problems associated with shrinkage stress from current resin systems, such as interfacial bonding failure, microleakage and recurrent caries.

The extremely high functional group conversion of thiol-ene polymers significantly mitigates the problems associated with the current dimethacrylate resin systems which is associated with the incomplete double bond conversion.

The thick cure depth and lack of oxygen inhibition of thiol-ene systems leads to one-step filling and curing during restorations, compared with the incremental filling technique using current dental resin systems.

The thiol-ene systems can be initiated by camphorquinone itself under visible light irradiation, without the presence of the amine accelerator.

The present invention may be thought of as a method of preparing a shaped dental prosthetic device for use in a human mouth. In the method, a mixture of first monomers and second monomers is dispensed wherein each first monomer has at least one thiol functional group and each second monomer has at least one vinyl functional group, and wherein 10% to 90% of the functional groups in the mixture are thiol functional groups. The mixture is shaped into the form of the shaped dental prosthetic device and then photopolymerized.

The present invention may also be thought of as a dental prosthetic device that incorporates a polymer created from the polymerization of a mixture of first monomers having thiol functional groups and second monomers having vinyl functional groups; wherein at least about 10% the functional groups of the polymer are thiol functional groups.

The present invention may also be thought of as a photopolymerizable dental restorative material comprising particles of filler; first monomers having thiol functional groups; second monomers having vinyl functional groups; and an initiator. In the photopolymerizable dental restorative material, at least about 10% of the functional groups in the dental restorative material are thiol functional groups.

The present invention may also be thought of as a photopolymerizable mixture comprising first monomers having thiol functional groups; second monomers having functional groups; and an initiator; wherein at least about 10% of the functional groups in the photopolymerizable mixture are thiol functional groups.

WRITTEN DESCRIPTION OF THE INVENTION

Figure 1:
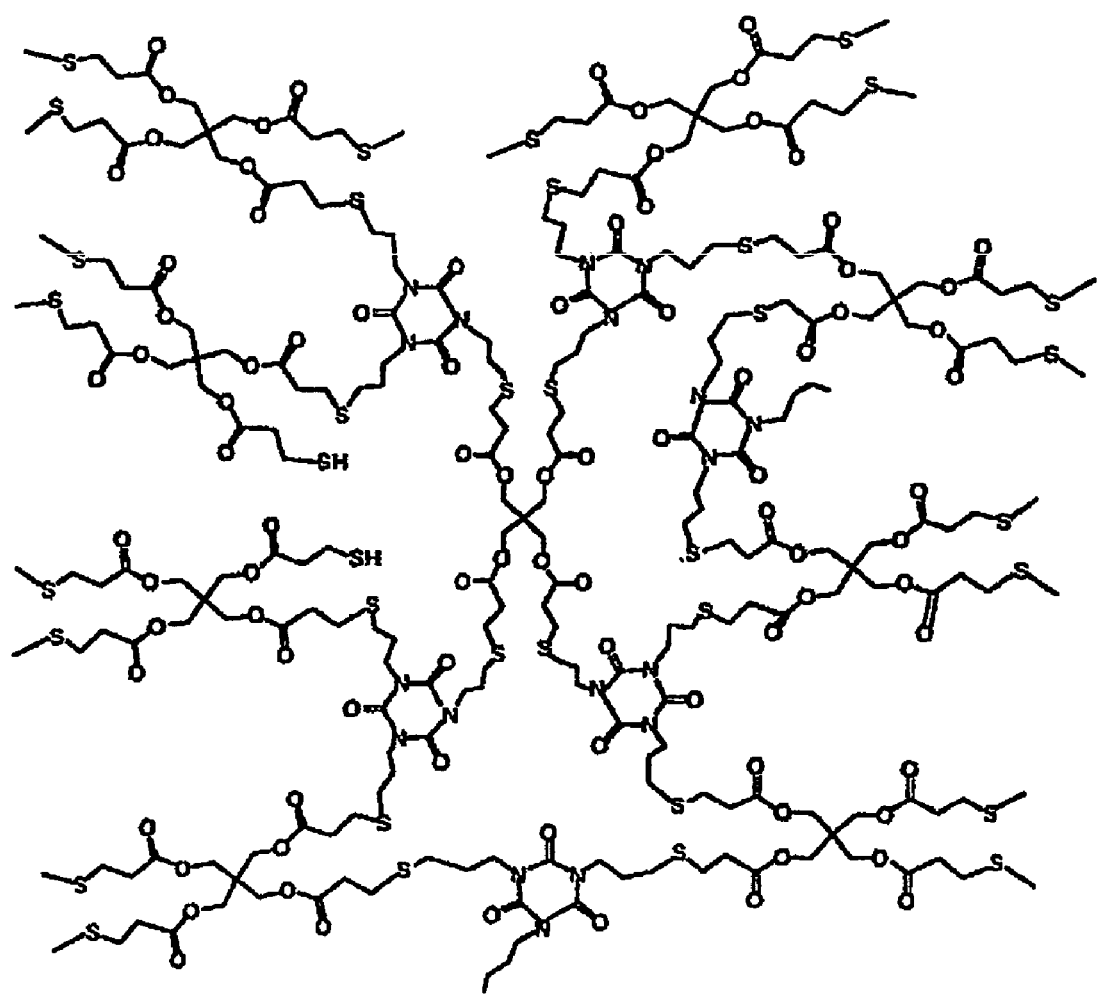
FIG. 1 illustrates a representation of a thiol-ene polymer created using PETMP/TATAO embodiment of the present invention.

Embodiments of the present invention are a thiol-ene polymer system. These systems have a high conversion, low shrinkage and low-shrinkage stress during curing. Embodiments of the thiol-ene system preferably has about 10%-90% of its functional groups as thiol functional groups, more preferably about 25%-60% thiol functional groups and even more preferably about 45%-55% thiol functional groups. The balance of the functional groups in the system may be vinyl functional groups. The vinyl functional groups may be provided by allyls, allyl ethers, vinyl ethers, acrylates or other monomers containing vinyl groups. For all of the embodiments studied containing multithiols and multivinyls of either allyls, allyl ethers or vinyl ethers, the polymerizations all achieved much higher conversions (than typical methacrylate systems) and reacted much more quickly to that conversion. In addition to thiols and vinyl functional groups, in some embodiments additional functional groups may be provided to tailor and provide additional properties.

Because of the step growth mechanism of the polymerization, for highest conversion it is preferred to have approximately equal amounts of initial functional groups (i.e., 50% thiol functional groups and 50% vinyl functional groups). For example, one preferred composition is pentaerythritol tetramercaptopropionate/Triallyl-1,3,5-triazine-2,4,6-trione (PETMP/TATATO) with a molar ratio of 3:4, or equal amount of SH and C=C groups.

Thiol bearing monomers suitable for embodiments the present invention include any monomer having thiol (mercaptan or "SH") functional groups. Thiols are any of various organic compounds having the general formula RSH which are analogous to alcohols but in which sulfur replaces the oxygen of the hydroxyl group. Suitable monomers may have one or more functional thiol groups and be of any molecular weight. Examples of suitable thiol bearing monomers include: pentaerythritol tetramercaptopropionate (PETMP); 1-Octanethiol; trimethylolpropane tris (3-mercaptopropionate); Butyl 3-mercaptopropionate; 2,4,6-trioxo-1,3,5-triazina-triy (triethyl-tris (3-mercapto propionate); and 1,6-Hexanedithiol.

Monomers having "-ene" or vinyl functional suitable for embodiments the present invention include any monomer having one or more functional vinyl groups, i.e., reacting "C=C" groups. Examples of suitable vinyl group bearing monomers include: Triallyl-1,3,5-triazine-2,4,6-trione (TATATO); Triethyleneglycol divinyl ether (TEGDVE); Vinyl Acrylate; triethyleneglycol dimethacrylate; trimethylolpropane diallyl ether; and Dodecyl Vinyl ether (DDVE).

Thiol-ene systems may also include and/or utilize various initiators, fillers, and accelerators depending on the application. For example, if photopolymerization using visible light is desired, camphorquinone may be used as an initiator. Alternatively, if ultraviolet photopolymerization is desired, then 2,2-dimethoxy-2-phenylacetophenone (DMPA) may be used as an initiator. Amine accelerators may also be used, as well as other accelerators. However, embodiments of the thiol-ene system can be readily initiated by just camphorquinone, without the presence of the amine accelerator. This is largely beneficial to the biocompatibility of photo-cured dental composites since studies have shown that certain tertiary amine accelerators, such as N,N-dimethyl-p-toluidine, are carcinogenic and mutagenic.

The thiol-ene systems of the present invention have some significant and unique advantages compared with (meth) acrylate polymerizations, which are extremely beneficial for dental resin applications. These advantages include: high gel-point conversion which significantly decreases shrinkage stress; rapid polymerization rate and lack of oxygen inhibition; nearly complete consumption of low molecular weight reacting species due to the nature of the step-growth mechanism, which limits the amount of leachable species and exhibiting less perceptible odor; versatile kinetics and structure-property design based on tailoring the thiol-ene monomer chemistry.

Experimentation shows, for a tri-allyl/tetra-thiol system, gel point conversions of up to about 40% were observed.

Another advantage of thiol-ene systems is that they can replace existing methacrylate systems. Thiol-ene polymers can be mixed and applied in the same manner currently used by dentists using methacrylate systems. The thiol-ene systems can be mixed with fillers as is typical in methacrylate systems. Depending on the initiator used, existing light sources used to photopolymerize the methacrylate systems may also be used. Likewise, dental restorative materials using thiol-ene polymer systems may be supplied in single-dose capsules or syringes.

EXAMPLES

Experimental work on the thiol-ene polymer embodiments as dental restorative materials was performed to demonstrate the feasibility and advantages of these polymers over currently used dental restorative materials. More specifically, the following monomers were studied:

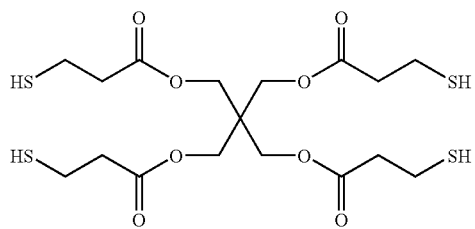

Pentaerythritol tetramercaptopropionate (PETMP)

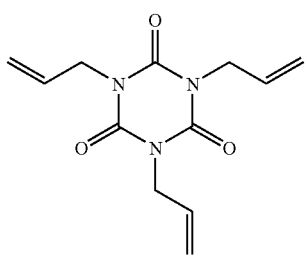

Triallyl-1,3,5-triazine-2,4,6-trione (TATATO)

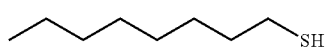

1-Octanethiol

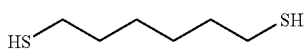

1,6-Hexanedithiol

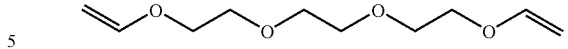

Triethyleneglycol divinyl ether (TEGDVE)

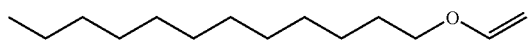

Dodecyl Vinyl ether (DDVE)

In addition, the following methacrylate system was used as a comparison:

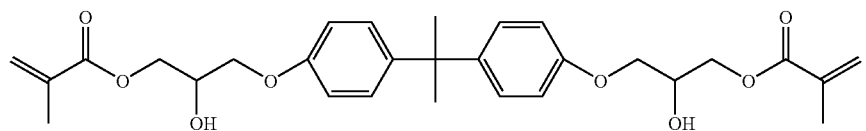

2,2-Bis[4-(2-hydroxy-3-methacryloyloxypropyloxy) phenyl]propane (Bis-GMA)

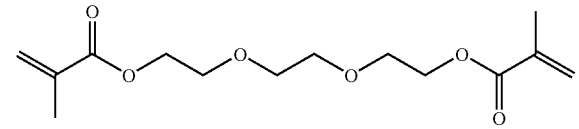

Triethyleneglycol dimethacrylate (TEGDMA)

The various systems above were polymerized under various conditions and the resulting polymers were tested. These included PETMP/TATATO (Molar ratio: 3:4); PETMP/VE1312 (Molar ratio: 3.4:4); PETMP/Bispheonl A Divinylether (DVEBPA) (Molar ratio 1:2); and 2,4,6-trioxo-1,3,5-triazina-triy (triethyl-tris (3-mercapto propionate) (T-BMPA)/VE1312 (Mol ratio: 3.4:3).

FIG. 1 illustrates a representation of an embodiment of a thiol-ene polymer created by polymerizing a mixture of PETMP/TATAO.

Polymerization Kinetics Investigation of Thiol-ene Systems

FTIR (Magna 750, Nicolet Instrument Corp., Madison, Wis.) was used to study the polymerization kinetics of the thiol-ene materials used in this study because of its inherent advantage of being able to measure the thiol and vinyl conversions simultaneously and rapidly. The infrared peak at 1643 per centimeter (cm$^{-1}$) was used for determining the allyl group conversion (of TATATO) and the peak at 2572 cm$^{-1}$ was used for the thiol group conversion.

Figure 2:
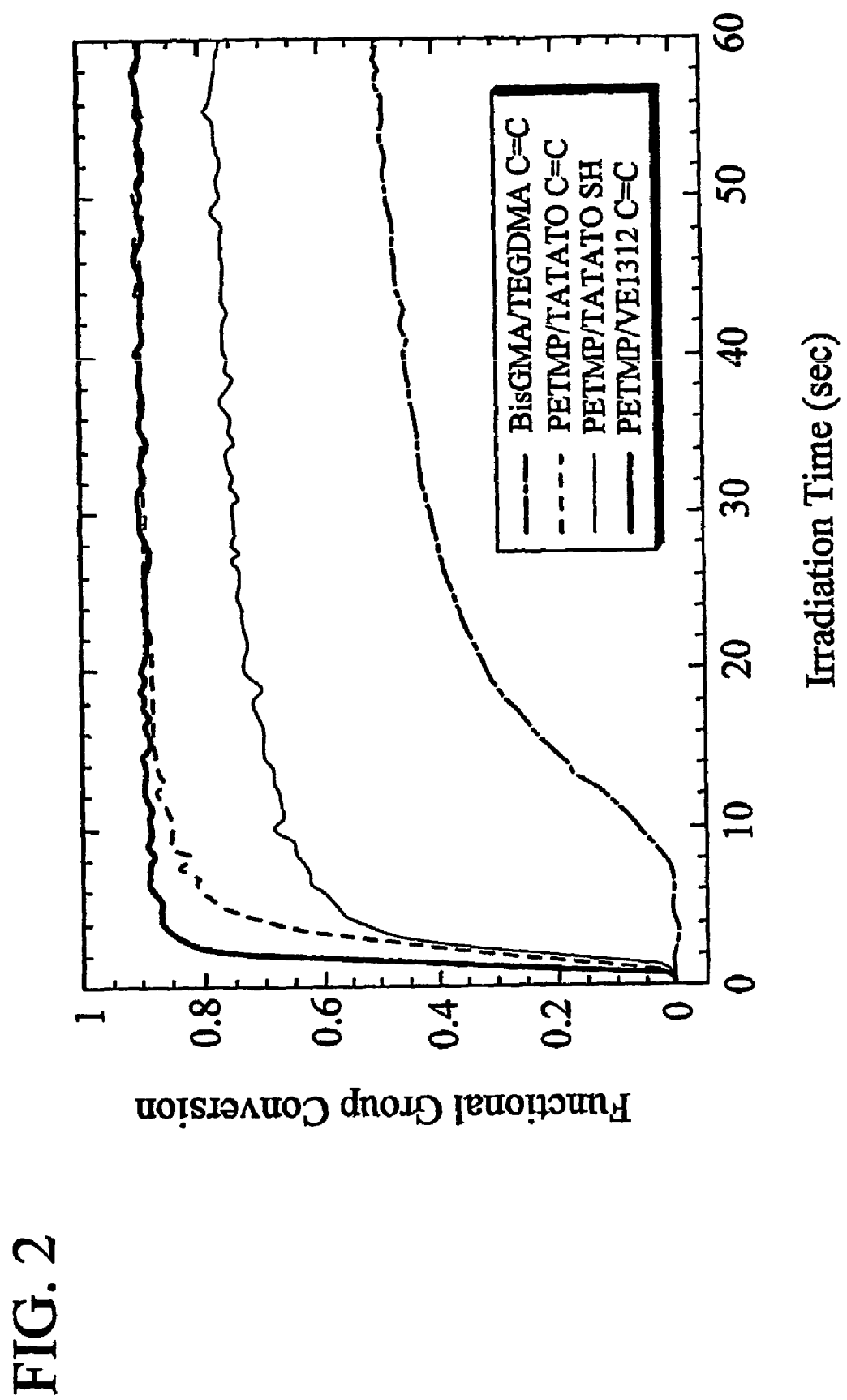
FIG. 2 is a plot of experimental conversion data showing the conversion of allyl and thiol functional groups of a PETMP/TATATO embodiment of the present invention and the conversion of the vinyl groups of a PETMP/VE1312 embodiment of the present invention; in comparison with the conversion of a typical Bis-GMA/TEGDMA (70/30 by wt.) as a function of irradiation time.

FIG. 2 is a plot of experimental conversion data showing the conversion of allyl and thiol functional groups of a PETMP/TATATO embodiment of the present invention; the conversion of the vinyl groups of a PETMP/VE1312 embodiment of the present invention; and the conversion of a non-thiol system Bis-GMA/TEGDMA (70/30 by wt.) as a function of irradiation time. In these experiments 0.1 wt % DMPA was used as an initiator. The polymer systems were cured using an ultraviolet irradiation intensity equal to 5.0 mW/cm$^2$ at a cure temperature (T$_{cure}$)=37° C. All thiol-ene monomer mixtures were prepared to have an equivalent concentration of the two functional groups.

As shown in FIG. 2, the polymerization of PETMP/TA-TATO occurs at a much higher rate than the typical dental restorative resin system Bis-GMA/TEGDMA (70/30 by wt.) cured under the same conditions. For each of the embodiments investigated, the conversion rate was such that at least about 90% of ultimate functional group conversion was achieved within 10 seconds. In the case of double bond conversion of the PETMP/TATATO embodiment, 90% of the ultimate double-bond functional group conversion was achieved within 8 seconds and 90% of the ultimate thiol functional group conversion was achieved within 10 seconds. For the PETMP/VE1312 embodiment of the present invention, 90% of the ultimate double-bond functional group conversion was achieved within approximately 3 seconds.

Also shown in FIG. 2, the final conversion of the allyl group was found to be approximately 90% and the thiol group final conversion was approximately 86%, while for Bis-GMA/TEGDMA the final conversion is only about 65%. The slight difference in the final conversion of the allyl and the thiol is caused by a small amount of homopolymerization that occurs with the allyl functional group.

The following is a list of polymerization kinetic results for various other thiol-ene systems studied. The polymerization conditions are the same as used in the experiments of FIG. 2 (0.1% DMPA; initial curing temperature at 37° C.; 5.0 mW/cm$^2$).

| System | Molar Ratio | Ultimate C=C Conversion | Ultimate SH Conversion | Time to Maximum Polymerization Rate (s) |
|---|---|---|---|---|
| PETMP/TATATO | 3:4 | 90% | 85% | 1.2 |
| PETMP/VE1312 | 3.4:4 | 91% | 93% | 0.7 |
| PETMP/DVEBPA | 1:2 | 78% | 80% | 2.1 |
| T-BMPA/VE1312 | 3.4:3 | 84% | 81% | 1.1 |

DVEBPA is Bispheonl A divinylether (a di-vinylether);
T-BMPA is 2,4,6-trioxo-1,3,5-triazina-triy(triethyl-tris(3-mercapto propionate)) (a tri-thiol).

In addition to the PETMP/TATATO system, a vinyl ether oligomer was copolymerized with the PETMP to evaluate the relative performance of vinyl ether. VEctomer® VE1312 (Morflex Inc., Greensboro, N.C.), a multifunctional vinyl ether containing a multifunctional polyester backbone, was used for this experiment. VE1312 has a number average molecular weight of 1250 g/mol, with average functionality of 3.4. Clearly, the combination of oligomerizing the vinyl group and changing to the vinyl ether increased the polymerization rate significantly. For all of the commercial systems studied containing multithiols and multivinyls of either allyls, allyl ethers or vinyl ethers, the polymerizations all achieved much higher conversions and reacted much more quickly to that conversion.

The experimentation shows that, in addition to higher conversion, dramatically reduced oxygen inhibition has been observed for all the thiol-ene polymerizations, as shown in FIG. 2. Although the experiment discussed above used ultraviolet light to simplify the initiating system, other experiments have also demonstrated that camphorquinone by itself readily initiates these polymerizations without the presence of an amine accelerator.

Material Properties Investigation of Commercial Thiol-ene Systems

Figure 3:
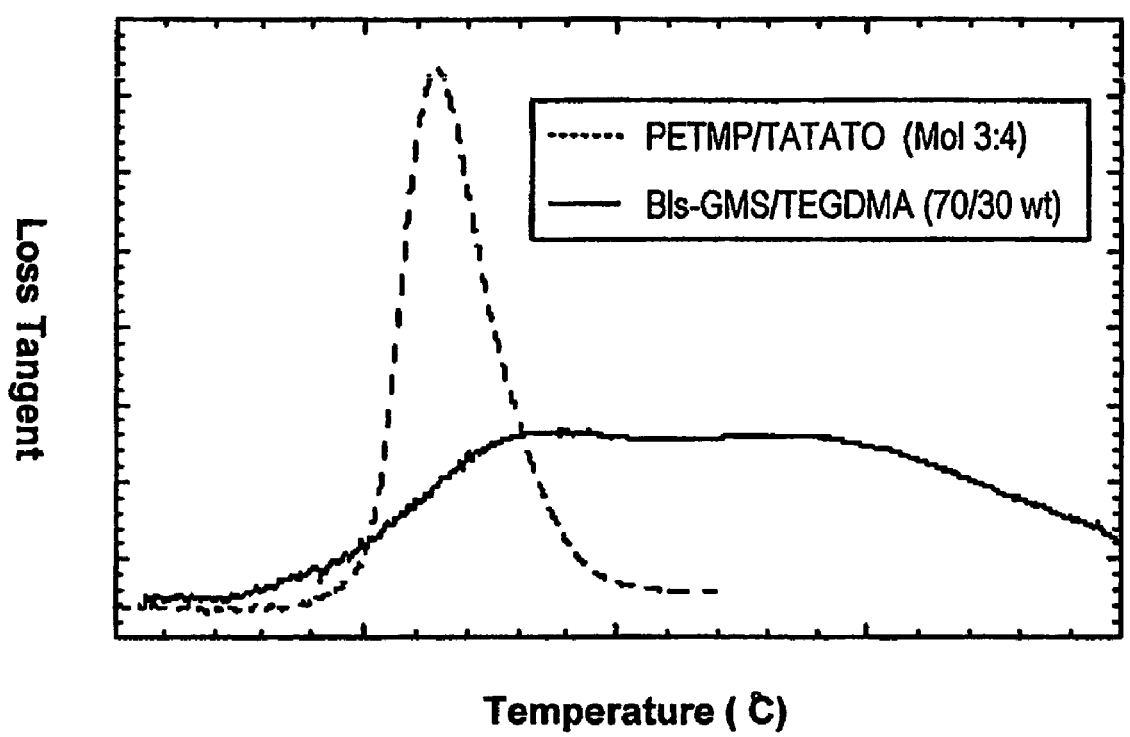
FIG. 3 is a plot of the loss tangent as a function of temperature for PETMP/TATATO (Molar ratio: 3:4) and Bis-GMA/TEGDMA (Mass ratio: 7:3) polymer.

In addition to the kinetics, various material property measurements were performed. Specimens for dynamic mechanical analysis (DMA) testing were photocured for 10 min with 10.0 mW/cm$^2$ of UV light at ambient conditions. A DMA7e (Perkin-Elmer, Norwalk, Conn.) was used to measure the glass transition temperature, T$_g$, of a PETMP/TATATO embodiment of the present invention. DMA was conducted over a temperature range of −50~120° C. with a ramping rate of 5° C. using extension mode (sinusoidal stress of 1 Hz frequency) and the loss tangent peak was monitored as a function of temperature as shown in FIG. 3. The loss tangent is defined as the polymer's loss modulus divided by storage modulus. During a DMA test, loss tangent peak corresponds to the viscoelastic relaxation of polymer chain or segments. Normally, the largest loss tangent peak can be associated with the polymer's glass transition peak and the temperature of the loss tangent peak maximum was used to define T$_g$ (glass transition temperature). For this sample, the glass transition temperature was found to be approximately 64° C. Each sample for the property measurement was prepared with an equal molar ratio of thiol functional groups to vinyl functional groups and was monitored with near infrared spectroscopy. Under these conditions, the vinyl group conversion was found to be approximately 90% in all cases.

For the flexural strength studies, monomer samples were photopolymerized in a Teflon® mold (specimen dimensions: 25±2 mm×2±0.1 mm×2±0.1 mm) with 580 mW/cm$^2$ visible light for 30 s on each side. Five specimens were prepared for each sample. A 3-point flexural test was carried out with a MTS® 858 Mini Bionix system (MTS Systems Corporation, Eden Prairie, Minn., USA) using a span width of 20 mm (10 mm for PETMP/TATATO embodiments) and a crosshead speed of 1 mm/min. The flexural strength (σ) and flexural modulus (E$_f$) in MegaPascals (MPa) were calculated using the following equations:

$$\sigma = \frac{3Fl}{2bh^2} \quad (1)$$

$$E_f = \frac{F_1 l^3}{4bh^3 d} \quad (2)$$

where F is the peak load (in N), l is the span length (in mm), b is the specimen width (in mm), h is the specimen thickness (in mm); and d is the deflection (in mm) at load F$_1$ (in N) during the straight line portion of the trace (ISO/DIS 4049, 1987). ISO/DIS 4049 is the international standard for "Dentistry—Polymer-based filling, restorative and luting materials". Flexural strength test is one of the tests specified in this standard for the polymer-based filling, restorative and luting materials.

As shown in Table 1, the flexural strength and flexural modulus of PETMP/TATATO are found to be 71.4±2.7 MPa and 1.6±0.3 GPa, respectively. Compared with the flexural strength of 93.2±8.3 MPa and flexural modulus of 2.6±0.1 GPa for Bis-GMA/TEGDMA system, this result indicates that the mechanical properties of PETMP/TATATO are not as high as current Bis-GMA/TEGDMA control system. However, it still exceeds the requirements for flexural strength test specified in ISO/DIS 4049. Furthermore, the quartz glass filled PETMP/TATATO system exhibits greater improvement in flexural strength and flexural modulus compared with Bis-GMA/TEGDMA system filled with the same amount of filler (Table 1).

TABLE 1

Flexural strength test results for filled and unfilled PETMP/TATATO and Bis-GMA/TEGDMA. Both resin systems contain 0.3 wt % CQ and 0.8 wt % EDAB as visible light initiator. For filled systems, 60 wt % silanized quartz filler (mean particle size of 5 μm) was used. All samples were cured with 580 mW/cm² visible light for 30 s on each side (n = 5).

| System | Flexural Strength (MPa) | Flexural Modulus (GPa) | Strain at Break (%) |
|---|---|---|---|
| PETMP/TATATO (Mol 3:4) | 71.4 ± 2.7 | 1.6 ± 0.3 | 11.7 ± 0.9 |
| PETMP/TATATO/Filler | 112.0 ± 8.0 | 5.4 ± 0.7 | 3.9 ± 0.8 |
| BisGMA/TEGDMA (Mass 7:3) | 93.2 ± 8.3 | 2.6 ± 0.1 | 7.1 ± 2.4 |
| BisGMA/TEGDMA/Filler | 125.8 ± 7.3 | 7.5 ± 0.5 | 2.1 ± 0.3 |

In addition to measuring the flexural strength and glass transition temperature of the model thiol-ene system, extraction studies were performed. As per Stansbury et al. each specimen was weighed immediately following polymerization. Soxhlet extraction of each specimen was conducted for 10 hours at 60° C., with dichloromethane used as the solvent. The mid-IR spectrum of the solvent after extraction was obtained and compared with that of the pure dichloromethane. No change in the infrared spectrum of the extracting dichloromethane was observed when compared with the pure dichloromethane. Also, no detectable substance was found following rotary evaporation of the extracting dichloromethane. After extraction, each specimen was dried to constant mass under 20 inch Hg vacuum at 60° C. For the thiol-ene samples this process took approximately 60 hours, and the average weight loss of the dried specimens was found to be from 0.4% to 0.6% relative to the original mass before extraction. This number compares extremely well with 11% extraction loss in a typical Bis-GMA/TEGDMA control sample polymerized under similar conditions to 68% methacrylate conversion. The number also compares reasonably well with the prediction for the amount of unreacted monomer remaining in the system, i.e., the amount of unreacted thiol or ene functional groups. Using the observed 86% thiol conversion and 90% vinyl conversion, the fraction of thiol monomer unreacted is calculated as (for the tetrathiol monomer) $(1-0.86)^4=0.04\%$ and the fraction of unreacted vinyl monomer is calculated as (for the trivinyl monomer) $(1-0.9)^3=0.1\%$. Thus, it was not expected that there would be a significant amount of extractable material at these conversions, which was verified by the experiments.

Figure 4:
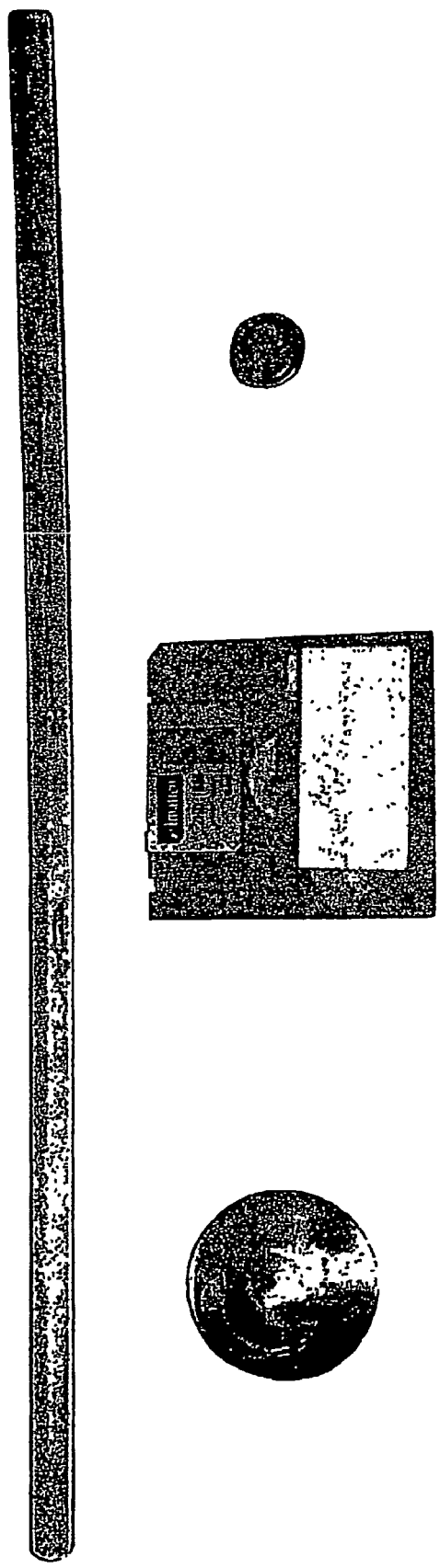
FIG. 4 is a photograph of a ball and a rod formed of embodiments of the present invention.

Finally, to demonstrate physically some of the advantages of thiol-ene polymers, large, stress-free samples were prepared by photopolymerization of embodiments of the present invention. These polymers include a 20 inch long rod that was polymerized from the top and a solid ball that was also polymerized from the top. The ball is approximately two inches in diameter. Each of these materials had minimal shrinkage, and more importantly, remained uncracked throughout the polymerization due to the minimal polymerization shrinkage stress. These samples are presented in FIG. 4.

Polymerization Volume Shrinkage of Thiol-ene Polymers

For samples such as many of the thiol-ene polymerizations that are lower viscosity and have relatively high gel point conversions, it is necessary to develop a different methodology for volume shrinkage measurements. For these systems, a straightforward method to measure the volume shrinkage was applied: measure the initial volume before polymerization by measuring the long dimension in a narrow, constant diameter tube, photo-cure the monomer, and then measure the final volume after polymerization by measuring the long dimension again. This technique is especially useful in studying the shrinkage of the stepwise-polymerized linear or crosslinking system, the latter has a much delayed gel-point and is therefore inappropriate to study using linometer or strain gauge. By using this approach, the volume shrinkage of thiol-vinyl ether and thiol-(triallyl-triazine-trione) embodiments of the present invention was investigated. Interestingly, the molar volume change for C=C bonds during polymerization are much lower than the acrylate or methacrylate systems, which produce 22.5~23 ml of shrinkage for every mole of double bond polymerized. Table 2 showed the results of this volume shrinkage study. Thus, it is not only the dramatic increase in gel point conversion that reduces the shrinkage stress in this system, but also the fact that each double bond that reacts leads to approximately half of the shrinkage that occurs in a traditional free radical polymerization.

TABLE 2

Volume shrinkage measurement using static volume change method

| System | Volume Shrinkage (%) | Molar Volume Change for C=C (ml/mol) |
|---|---|---|
| MMA (Patel et at. 1983) | 20.6 | 22.5 |
| HDT/TEGDVE (Molar Ratio: 1:1) | 7.1 | 12.7 |
| OT/DDVE (Molar Ratio: 1:1) | 2.9 | 12.6 |
| OT/TATATO (Molar Ratio: 3:1) | 6.1 | 15.1 |

MMA: Methyl methacrylate;
HDT: 1,6-Hexanedithiol;
TEGDVE: Triethylene glycol di(vinyl ether);
OT: 1-Octanethiol;
DDVE: Dodecyl vinyl ether;
TATATO: Triallyl-1,3,5-triazine-2,4,6-trione.

Simultaneous Measurement of Thiol-ene Shrinkage Stress and Conversion

Figure 5:
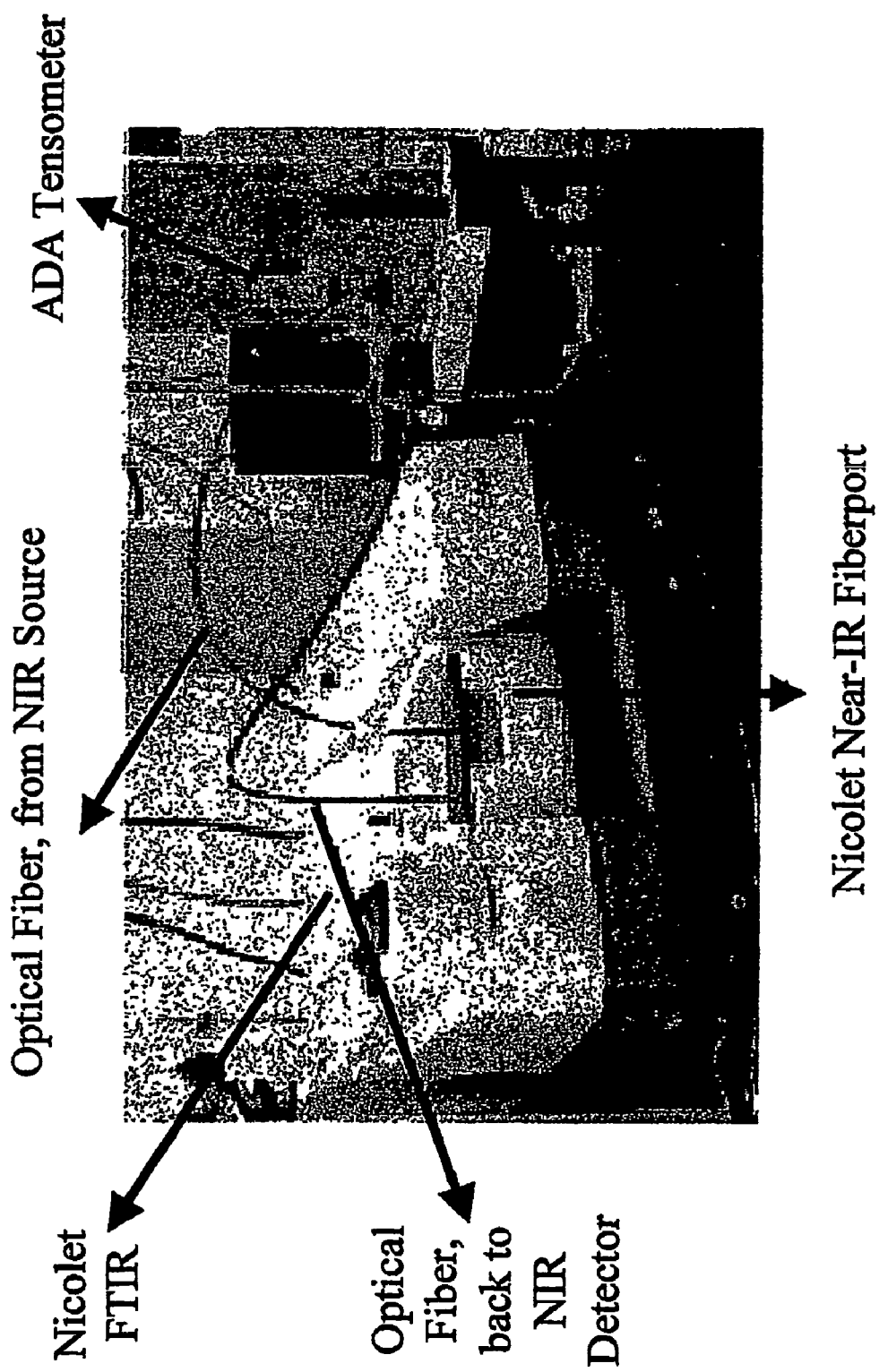
FIG. 5 is a photograph of an experimental device capable of simultaneous measurement of the shrinkage stress and conversion of a sample during polymerization.

This experimental set-up is capable of simultaneous measurement of the shrinkage stress and conversion, both on exactly the same sample at the same time. The in situ, real-time monitoring of the polymerization was achieved by guiding the near-IR beam through the sample, which was mounted on the tensometer, then refocusing the transmitted signal to the near-IR detector. The tensometer, designed by American Dental Association (ADA), is based on the cantilever beam deflection theory: shrinkage force generated by the composite during curing causes the beam to bend, and the deflection is measured with a linear variable differential transformer (LVDT). The shrinkage force is then calculated using the beam constant of the cantilever beam. Therefore, the shrinkage stress value is obtained by dividing the shrinkage force by the composite sample cross-sectional area. With the combination of different beam lengths and materials, it is possible to measure the shrinkage stress accurately over a wide range of values. FIG. 5 presents a photograph of this novel experiment set-up.

Figure 6:
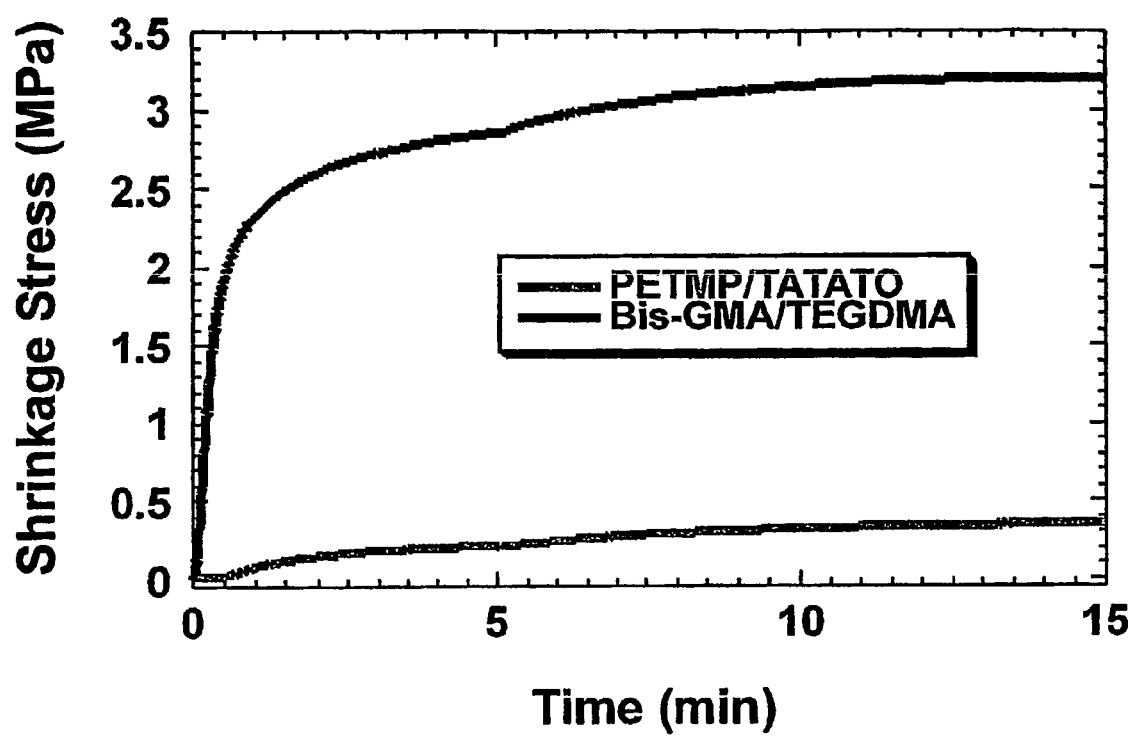
FIG. 6 is a plot of shrinkage stress as a function of time for a typical Bis-GMA/TEGDMA polymer and a PETMP/TATATO embodiment of the present invention.

Using the combined tensometer and remote near-IR technique, the simultaneous shrinkage stress and conversion of Bis-GMA/TEGDMA and PETMP/TATATO were measured from the same sample at the same time. As shown in FIG. 6, the final shrinkage stress achieved by a PETMP/TATATO embodiment of the present invention is less than 12% of the Bis-GMA/TEGDMA system, both cured under identical conditions of visible light irradiation intensity of 330 mW/cm² for 5 min at room temperature.

Figure 7:
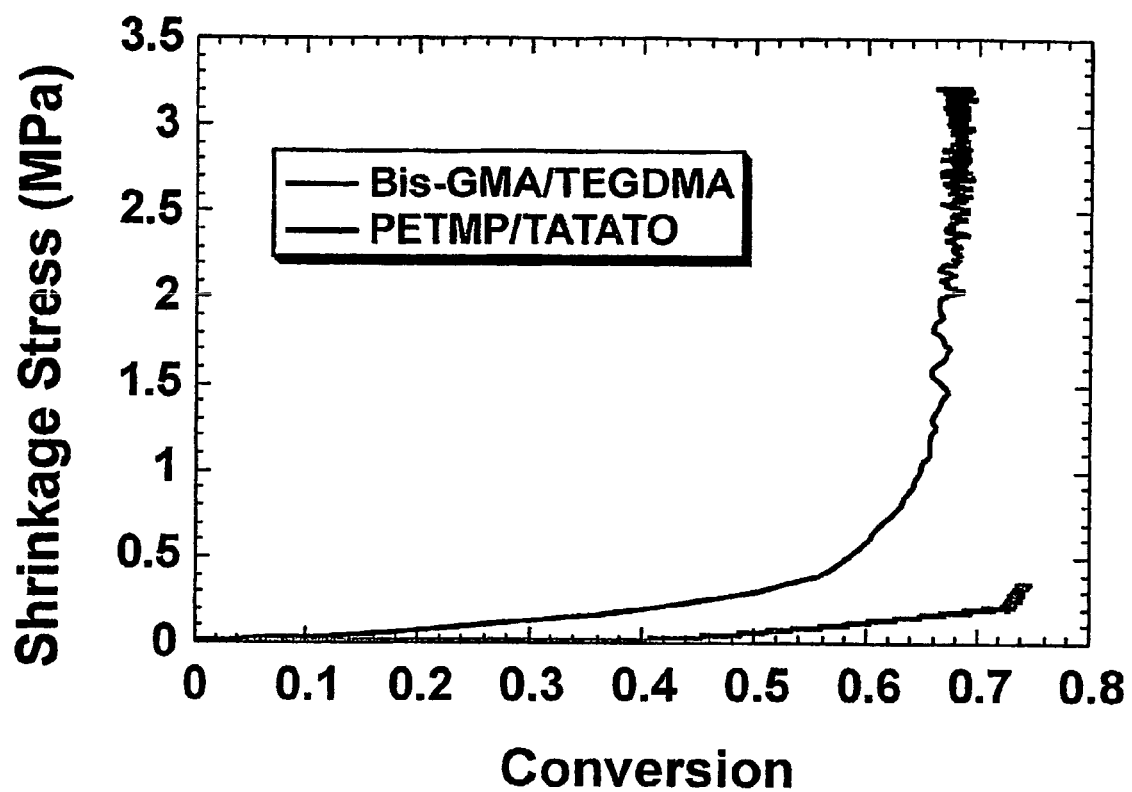
FIG. 7 is a plot of the shrinkage stress as a function of double bond conversion for the systems of FIG. 6.

The extremely low shrinkage stress of thiol-ene polymers resulted from not only the relatively high gel point conversion but reduced volume shrinkage that each double bond generates during polymerization. A plot of the shrinkage stress as a function of double bond conversion is shown in FIG. 7. It further illustrated the advantages of thiol-ene polymers for dental restorative materials: dramatically reduced shrinkage stress and improved functional group conversion.

Figure 8:
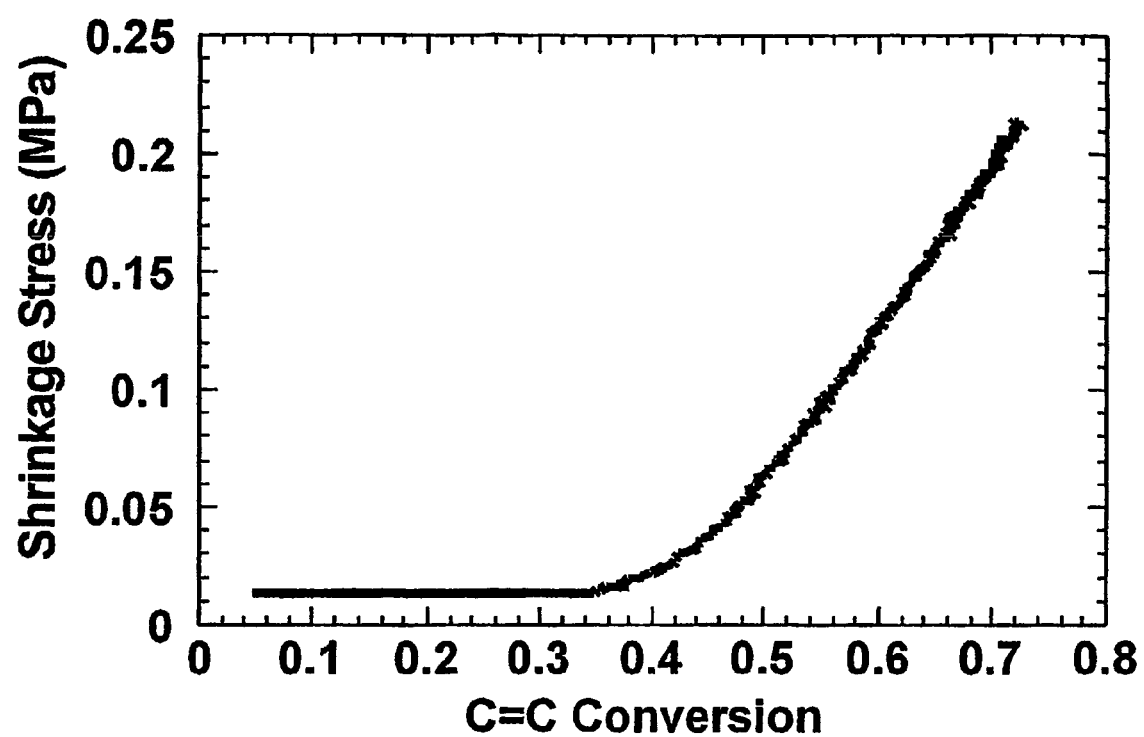
FIG. 8 is a plot of the shrinkage stress as a function of double bond conversion for another PETMP/TATATO embodiment of the present invention.

The simultaneous shrinkage stress as a function of double bond conversion for another embodiment (PETMP/TATATO system with 0.5 wt % CQ cured using 375 mW/cm$^2$ visible light) is shown in FIG. 8. It can be seen that shrinkage stress did not start to build up until approaching the gel point conversion (theoretical gel point $f_c$=40.8% for this system). This agrees very well with the prediction that any volume shrinkage that occurred before the gel point will not result in shrinkage stress, as the shrinkage can be readily accommodated by the flow of the liquid mixture of oligomers. The maximum shrinkage stress developed was about 0.21 MPa, which was less than 10% of the maximum shrinkage stress of the Bis-GMA/TEGDMA system cured under the same conditions.

Synthesis of Reactive Oligomeric Thiol and ene Materials

The purposes of synthesizing oligomeric thiol and ene materials are to optimize both polymer properties and polymerization performance and eliminate odor concerns. Because of the step growth nature of the thiol-ene photopolymerization, it is possible to oligomerize (both synthetic and commercially available) monomers to a significantly higher extent of polymerization prior to formulating the materials and completing the polymerization in the restoration. This technique is expected to have enormous advantages over the low molecular weight embodiments of the present invention studied herein. First, since the overall functional group concentration will be decreased dramatically, the shrinkage will correspondingly be decreased while still maintaining the identical ultimate network structure and material properties. Secondly, with higher molecular weight thiols, it will be more facile to purify the oligomers and remove the trace, low molecular weight compounds responsible for the odor in these systems and to limit further the amount of extractables.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

We claim:

1. A photopolymerizable dental restorative material consisting essentially of: particles of filler; first monomers having thiol functional groups; second monomers having vinyl functional groups; an initiator selected from camphorquinone or 2,2-dimethoxy-2-phenylacetophenone; and an optional amine accelerator; wherein at least about 10% of the functional groups in the dental restorative material are thiol functional groups; and wherein the material does not contain an additional initiator; and wherein, upon exposure to light, the material cures without oxygen inhibition; and wherein after polymerization the material exhibits a flexural strength of greater than 100 Mega Pascals.

2. The photopolymerizable dental restorative material of claim 1, wherein at least about 15% to about 60% of the functional groups in the dental restorative material are thiol functional groups.

3. The photopolymerizable dental restorative material of claim 1, wherein at least about 45% to about 55% of the functional groups in the dental restorative material are thiol functional groups.

4. The photopolymerizable dental restorative material of claim 1 that when polymerized exhibits a volume shrinkage of less than 10%.

5. The photopolymerizable dental restorative material of claim 1 that when polymerized creates a polymer having an average weight loss, when dried, of 0.4 to 0.6% relative to an original mass before extraction.

6. The photopolymerizable dental restorative material of claim 1 that when polymerized creates a polymer having a shrinkage stress of less that 3.0 MPa.

7. The photopolymerizable dental restorative material of claim 1 that when polymerized creates a polymer having a shrinkage stress of less that 1.5 MPa.

8. The photopolymerizable dental restorative material of claim 1 that when polymerized creates a polymer having a shrinkage stress of less that 0.5 MPa.

9. The photopolymerizable dental restorative material of claim 1, which is curable with visible light, wherein the initiator is camphorquinone.

10. The photopolymerizable dental restorative material of claim 9, containing an amine accelerator.

11. The photopolymerizable dental restorative material of claim 10, wherein the amine accelerator is ethyl 4-(dimethylamino)benzoate.

12. The photopolymerizable dental restorative material of claim 1, which is curable with ultraviolet-light, wherein the initiator is 2,2-dimethoxy-2-phenylacetophenone.

* * * * *